United States Patent
Erickson et al.

(10) Patent No.: US 6,767,098 B2
(45) Date of Patent: Jul. 27, 2004

(54) OPHTHALMOSCOPIC PRISM

(75) Inventors: Phillip J. Erickson, Medina, WA (US); Paul C. Whalen, Maple Valley, WA (US); Peter G. Harrington, Seattle, WA (US); Raymond D. Graham, Renton, WA (US)

(73) Assignee: Ocular Instruments, Inc., Bellevue, WA (US)

( * ) Notice: Subject to any disclaimer, the term of this patent is extended or adjusted under 35 U.S.C. 154(b) by 40 days.

(21) Appl. No.: 10/232,557

(22) Filed: Aug. 29, 2002

(65) Prior Publication Data

US 2004/0041979 A1 Mar. 4, 2004

(51) Int. Cl.[7] ................................................ A61B 3/00
(52) U.S. Cl. ...................................................... 351/219
(58) Field of Search ............................. 351/205, 219, 351/220, 221, 245, 246, 247

(56) References Cited

U.S. PATENT DOCUMENTS

| | | |
|---|---|---|
| 4,033,679 A | 7/1977 | Sussman |
| 4,598,984 A | 7/1986 | Rol |
| 5,537,164 A | 7/1996 | Smith |
| 5,784,147 A | * 7/1998 | Volk ........................... 351/219 |

* cited by examiner

Primary Examiner—George Manuel
(74) Attorney, Agent, or Firm—Christensen O'Connor Johnson Kindness PLLC

(57) ABSTRACT

An ophthalmoscopic prism, for example a gonioscope, has an optically transparent body, the distal end carries a viewing surface preferably oriented perpendicularly to the optical axis of the body, the proximal end of the prism carries a concave surface having a curvature similar to the curvature of the cornea of a patient. The proximal end has at least one planar surface extending outwardly and distally from a location adjacent the periphery of the concave surface. The body has an index of refraction that provides total internal reflection to a viewer looking through the viewing surface even when the planar surface is at least partially wetted with a fluid.

11 Claims, 2 Drawing Sheets

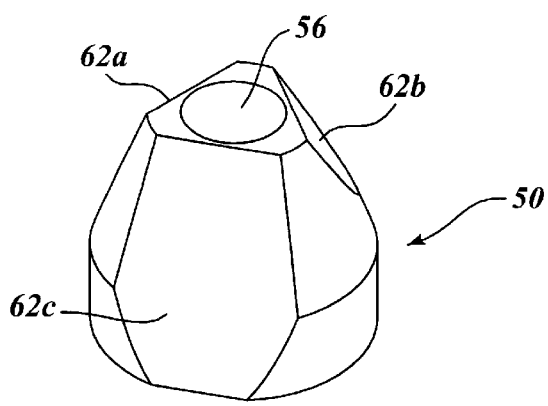
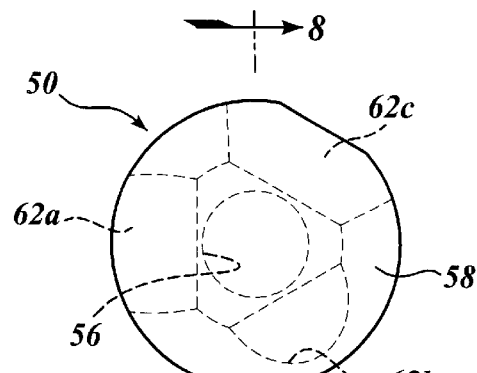
Fig.6.
Fig.7.
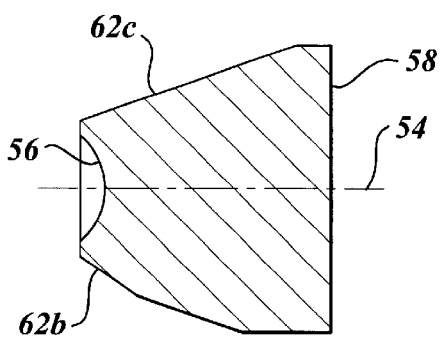
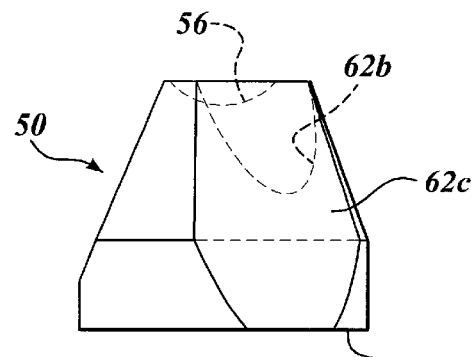
Fig.8.
Fig.9.
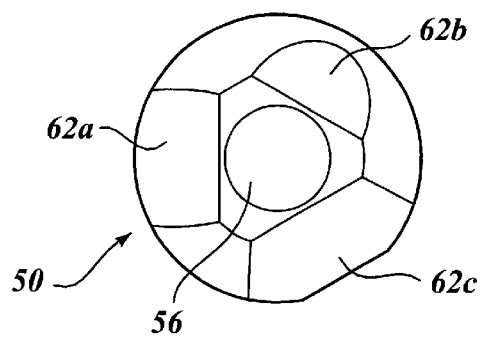
Fig.10.

OPHTHALMOSCOPIC PRISM

FIELD OF THE INVENTION

The present invention relates to ophthalmic lenses and prisms and more particularly to an ophthalmoscopic prism utilized in the diagnosis and treatment of the eye.

BACKGROUND OF THE INVENTION

Gonioscopes or ophthalmoscopic prisms are used for viewing the angle of the trabeculum, the drainage angle, and related structures of the eye. A gonioscope traditionally used is disclosed in U.S. Pat. No. 4,033,679 to Dr. Walter Sussman. This gonioscope comprises a cylindrical optical body having at its proximal end four planar, inclined facets that narrow toward the proximal end. The planar facets are inclined from 20 degrees to 40 degrees relative to the optical axis of the body. The distal end of the lens has a viewing surface that is substantially perpendicular to the optical axis of the cylinder. The proximal end of the lens has a concave surface with its optical center on the optical axis of the lens. The planar facets have a mirrored coating thereon.

The concave surface is designed to be placed in contact with the cornea of a patient. When the ophthalmologist looks through the viewing surface, the internal surface of the facets totally reflects so that the ophthalmologist can for example see the trabeculum. If it were not for this reflective coating, moisture in contact with the planar surfaces would also be seen by the ophthalmologist thus impairing, for example, his view of the trabeculum. In addition, prisms of this type contain additional coatings to protect the reflective coating and many times are required to be housed in holders to prevent damage to the coatings or mirrored surfaces. Finally, prior gonioscopes are made from optical materials such as methylmethacrylate, or have protective surface coatings, and thus are not autoclavable.

SUMMARY OF THE INVENTION

The present invention provides an ophthalmoscopic prism that cannot only be autoclaved but also does not require the reflective and protective coatings required of the prior art prisms. The present invention includes an optically transparent body having an optical axis. The distal end of the transparent body has a viewing surface oriented transversely to the optical axis. The proximal end of the body has a concave surface having a curvature complimentary to the curvature of the cornea of a patient. The proximal end of the body has at least one planar surface extending outwardly and distally from a location adjacent the periphery of the concave surface. In addition, the body has an index of refraction that provides total internal reflection when a viewer looks through the viewing surface, even when the planar surface is at least partially wetted with a fluid.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 6 is an isometric view of a second embodiment of a prism constructed in accordance with the present invention having planar surfaces with varying angles;

FIG. 7 is a view of the distal end of the prism of FIG. 6;

FIG. 8 is a cross-sectional view of the prism of FIG. 7 taken along section line 8—8;

FIG. 9 is an elevation view of the prism of FIG. 6; and

FIG. 10 is a view of the proximal end of the prism of FIG. 6.

DETAILED DESCRIPTION OF THE PREFERRED EMBODIMENT

Figure 1:
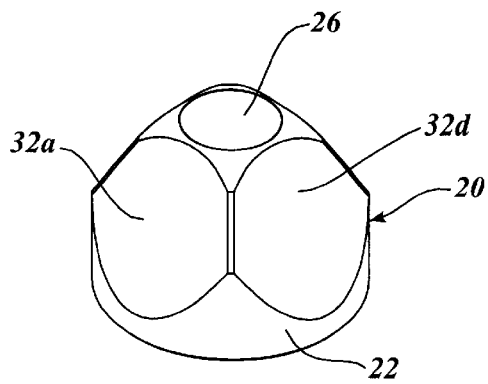
FIG. 1 is an isometric view of a gonioscope constructed in accordance with the present invention.
Figure 2:
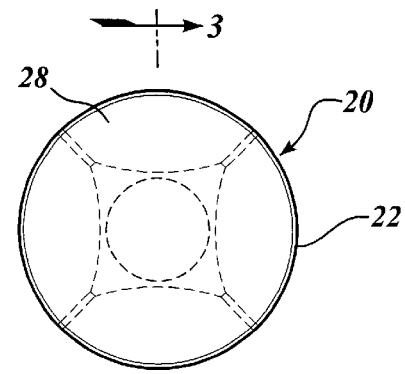
FIG. 2 is a view of the distal end of the prism of FIG. 1.

Referring to FIGS. 1–5, an ophthalmoscopic prism 20 is constructed in accordance with the present invention to function as a gonioprism for use by ophthalmologists in viewing the trabecular meshwork and related adjacent structures in the eye. The prism 20 has a body 22 composed of an optically transparent material having an index of refraction ranging in accordance with the present invention of about 1.57, or greater, and more preferably 1.72 or greater. It is preferred that the body be composed of an optical grade glass, although certain polymeric materials may be employed provided they exhibit the required index of refraction. The prism 20 has an optical axis 24 about which the structure is constructed and defined. The proximal end of the prism, that is the end nearest the eye of a patient, has formed therein a concave surface 26 centered on the optical axis 24. The curvature of the concave surface 26 is similar to the convex curvature of the typical cornea of a patient. A typical radius of curvature for the concave surface would be on the order of 8 mm. Of course, other radii of curvature could be employed as desired or as necessary.

The distal end of the lens carries a viewing face 28. The viewing face 28 may be transverse to the optical axis 24, but is preferably orthogonal to the optical axis. The face may be planar or if desired can carry a spherical or aspherical curvature to increase the power of the optics and thus provide any desired magnification.

Figure 3:
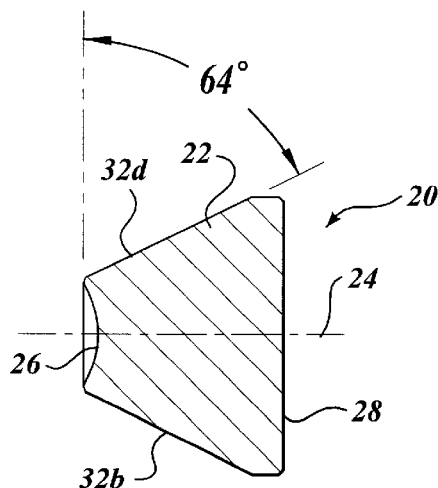
FIG. 3 is a longitudinal sectional view taken along section line 3—3 of FIG. 2.
Figure 4:
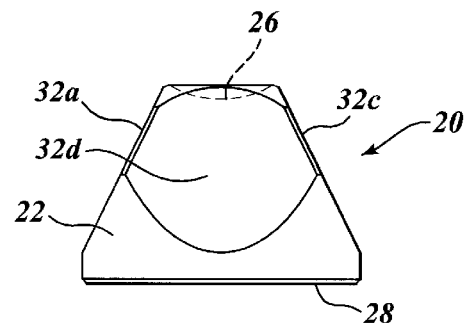
FIG. 4 is an elevation view of the prism of FIG. 1.
Figure 5:
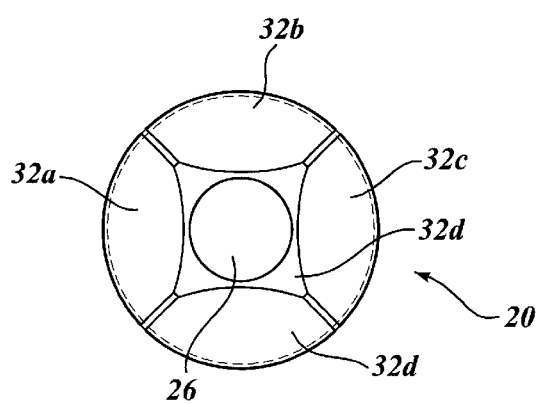
FIG. 5 is a view of the proximal end of the prism of FIG. 1.

In this preferred embodiment, the gonioprism has four planar faces 32a, 32b, 32c and 32d formed on the sides of the body 22. The faces or facets 32a through 32d extend from a location adjacent the proximal end of the body and the periphery of the concave surface 26, and extend radially outwardly and at the same time in a distal direction relative to the optical axis 24. The four faces are equally spaced in each quadrant of the body 22 and terminate short of the distal end and distal viewing face 28 of the lens. In this embodiment, the planar surface of each of the faces makes an angle of approximately 64 degrees relative to a plane orthogonal to the optical axis 24 as shown in FIG. 3. This angle may be varied depending upon the particular location in the eye that is desired to be observed by the ophthalmologist. The preferred angle is 64 degrees if the trabecular meshwork and related areas of the eye are to be viewed. However, as will be seen in conjunction with the alternate embodiment, this angle may be equal to or greater than 40 degrees, is preferably equal to or greater than 55 degrees, and most preferably is equal to or greater than 59 degrees, all relative to a plane orthogonal to the optical axis of the prism.

In accordance with the present invention, the index of refraction of the material comprising the body 22 must be sufficiently high so that total internal reflection is achieved by the facets 32a through 32d, even if the facets are wetted by eye fluid, wetting fluid, or optical coupling agents. The index of refraction required to achieve total internal reflection varies with the angle of the facet relative to a plane orthogonal to the optical axis. For example, as the angle becomes smaller, a larger index of refraction is required. For the lens just described above, it is preferred that the index of refraction be at least 1.72 or greater. With this index of refraction, no optical coating is required. It is preferred that the body be made from an optical glass with the desired index of refraction. Polymeric materials may also be used provided they are clear and exhibit the desired index of refraction. When the body 22 is composed of a suitable optical material, it is fully autoclavable as opposed to lenses of the prior art.

Referring now to FIGS. 6–10, a second embodiment of the invention is disclosed. In this embodiment, the prism 50 is designed to view the periphery of the fundus and the region toward the macula of the eye. In this embodiment, similarly to the prior embodiment, the proximal ends of the lens carries a concave surface 56 approximating the normal curvature of the cornea of the average patient. The viewing surface 58 is preferably orthogonal to the optical axis 54 of the prism 50. This lens differs from the prior lens in that it carries three facets 62a, 62b and 62c. These facets 62a through 62c extend from a location adjacent the periphery of the concave surface 56 distally and radially outwardly relative to the optical axis 54. In this lens, the facets 62a, 62b and 62c have angles of 67 degrees, 59 degrees and 73 degrees, respectively, relative to a plane orthogonal to the optical axis 54. For the facets that have angles that are greater than those of the prior embodiment (64 degrees), the optical material used for the prism may have an index of refraction that is less than that employed in the lens of FIGS. 1–5. However, for the facet that has an angle less than the prior embodiment, the index of refraction may be higher to achieve the desired result of total internal reflection even if wetted. For this lens, an index of refraction of 1.72 or greater is most preferred. In this embodiment, the facets 62a through 62c of the present invention need not be coated. Because of the high index of refraction of the material of the body 52, total internal reflection of the facets 62a through 62c is achieved even though the exterior surfaces of the facets are in contact with a liquid.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An ophthalmoscopic prism comprising:
   an optically transparent body having a optical axis, a distal end and a proximal end, said distal end having a viewing surface oriented transversely to said optical axis, said proximal end having a concave surface having a curvature that is similar to the curvature of the cornea of a patient, said proximal end having at least one planar surface extending outwardly and distally from a location adjacent the periphery of said concave surface, said body having an index of refraction that provides total internal reflection to a viewer looking through said viewing surface even when said planar surface is at least partially wetted with a fluid.

2. The ophthalmoscopic prism of claim 1 wherein said viewing surface is perpendicular to said optical axis.

3. The ophthalmoscopic prism of claim 1 wherein said planar surface has an angle greater than or equal to 40 degrees relative to a plane orthogonal to said optical axis.

4. The ophthalmoscopic prism of claim 1 wherein said planar surface has an angle greater than or equal to 55 degrees relative to a plane orthogonal to said optical axis.

5. The ophthalmoscopic prism of claim 1 wherein said planar surface has an angle greater than or equal to 59 degrees relative to a plane orthogonal to said optical axis.

6. The ophthalmoscopic prism of claim 1 wherein said index of refraction is at least 1.57.

7. The ophthalmoscopic prism of claim 1 wherein said index of refraction is at least 1.72.

8. The ophthalmoscopic prism of claim 1 wherein said body is comprised of an autoclavable material.

9. The ophthalmoscopic prism of claim 1 wherein said body comprises optical glass.

10. The ophthalmoscopic prism of claim 1 wherein said planar surface is uncoated.

11. The ophthalmoscopic prism of claim 1 wherein said proximal end has more than one planar surface extending distally and outwardly from a location adjacent the periphery of the concave surface.

\* \* \* \* \*